United States Patent
Stamp

(10) Patent No.: US 11,000,281 B2
(45) Date of Patent: May 11, 2021

(54) BONE STAPLE INSERTER

(71) Applicant: ORTHO SOLUTIONS HOLDINGS LIMITED, Littleton, CO (US)

(72) Inventor: Kevin Stamp, Sheffield (GB)

(73) Assignee: ORTHO SOLUTIONS HOLDINGS LIMITED, Littleton, CO (US)

( * ) Notice: Subject to any disclaimer, the term of this patent is extended or adjusted under 35 U.S.C. 154(b) by 223 days.

(21) Appl. No.: 16/227,788

(22) Filed: Dec. 20, 2018

(65) Prior Publication Data

US 2019/0192160 A1 Jun. 27, 2019

Related U.S. Application Data

(60) Provisional application No. 62/609,724, filed on Dec. 22, 2017.

(51) Int. Cl.
| | |
|---|---|
| *A61B 17/10* | (2006.01) |
| *A61B 17/064* | (2006.01) |
| *A61B 17/068* | (2006.01) |
| *A61B 90/00* | (2016.01) |
| *A61B 17/00* | (2006.01) |

(52) U.S. Cl.
CPC .......... *A61B 17/10* (2013.01); *A61B 17/0642* (2013.01); *A61B 17/0682* (2013.01); *A61B 2017/00367* (2013.01); *A61B 2017/00867* (2013.01); *A61B 2017/0645* (2013.01); *A61B 2090/0811* (2016.02)

(58) Field of Classification Search
CPC .............. A61B 17/10; A61B 17/00367; A61B 17/0642; A61B 17/0682; A61B 2017/0645; A61B 2017/00867
See application file for complete search history.

(56) References Cited

U.S. PATENT DOCUMENTS

| | | | |
|---|---|---|---|
| 5,497,933 A * | 3/1996 | DeFonzo | A61B 17/0684 227/175.1 |
| 5,695,524 A | 12/1997 | Kelley et al. | |
| 5,715,987 A | 2/1998 | Kelley et al. | |
| 6,059,787 A | 5/2000 | Allen | |
| 6,083,242 A | 7/2000 | Cook | |
| 6,348,054 B1 | 2/2002 | Allen | |
| 6,783,531 B2 | 8/2004 | Allen | |
| 8,235,995 B2 | 8/2012 | Focht et al. | |

(Continued)

FOREIGN PATENT DOCUMENTS

| | | |
|---|---|---|
| AU | 2013206096 B2 | 1/2014 |
| CA | 2817333 A1 | 12/2013 |

(Continued)

*Primary Examiner* — Robert F Long
*Assistant Examiner* — Xavier A Madison
(74) *Attorney, Agent, or Firm* — Hudak, Shunk & Farine Co. LPA

(57) ABSTRACT

The invention is an inserter for a staple having a bridge member and opposing open legs and the inserter holds the staple between a pair of cylindrical expanders which splay apart in response to a camming mechanism having a pair of followers that carry the expanders. The followers are activated as they are drawn over the camming ramp in response to a trigger action. The ramp also includes a detent which alerts the user that the staple is engaged in an activated position, and a safety that keeps the followers from returning to the un-loaded position.

17 Claims, 10 Drawing Sheets

(56) References Cited

U.S. PATENT DOCUMENTS

| | | |
|---|---|---|
| 8,584,853 B2 | 11/2013 | Knight et al. |
| 8,596,514 B2 | 12/2013 | Miller et al. |
| 8,721,646 B2 | 5/2014 | Fox |
| 8,808,294 B2 | 8/2014 | Fox et al. |
| 9,017,331 B2 | 4/2015 | Fox |
| 9,095,338 B2 | 8/2015 | Taylor et al. |
| 9,101,349 B2 | 8/2015 | Knight et al. |
| 9,204,932 B2 | 12/2015 | Knight et al. |
| D748,258 S | 1/2016 | Gledel |
| 2002/0173793 A1 | 11/2002 | Allen |
| 2010/0063506 A1 | 3/2010 | Fox et al. |
| 2012/0228355 A1 | 9/2012 | Combrowski et al. |
| 2013/0026206 A1 | 1/2013 | Fox |
| 2013/0041406 A1 | 2/2013 | Bear et al. |
| 2013/0206815 A1 | 8/2013 | Fox |
| 2013/0231667 A1 | 9/2013 | Taylor et al. |
| 2013/0331839 A1 | 12/2013 | Hester et al. |
| 2014/0014553 A1 | 1/2014 | Knight et al. |
| 2014/0018809 A1 | 1/2014 | Allen |
| 2014/0020333 A1 | 1/2014 | Knight et al. |
| 2014/0034702 A1 | 2/2014 | Miller et al. |
| 2014/0097228 A1 | 4/2014 | Taylor et al. |
| 2014/0277516 A1 | 9/2014 | Miller et al. |
| 2014/0358187 A1* | 12/2014 | Taber ............... A61B 17/0682 606/86 R |
| 2016/0235460 A1* | 8/2016 | Wahl ................ A61B 17/0682 |
| 2017/0100163 A1 | 4/2017 | Palmer et al. |
| 2017/0231625 A1* | 8/2017 | Handie .............. A61B 17/0642 227/175.1 |
| 2017/0281157 A1 | 10/2017 | Hartdegen et al. |
| 2018/0289366 A1 | 10/2018 | Morgan et al. |
| 2018/0353172 A1 | 12/2018 | Hartdegen et al. |
| 2019/0046182 A1* | 2/2019 | Krumme ........... A61B 17/0642 |
| 2019/0231349 A1 | 8/2019 | Wahl et al. |
| 2019/0282231 A1 | 9/2019 | Vasta |
| 2020/0000464 A1 | 1/2020 | Gaston et al. |
| 2020/0008807 A1 | 1/2020 | Hollis |
| 2020/0038076 A1 | 2/2020 | Amis et al. |
| 2020/0100820 A1 | 4/2020 | Hollis et al. |

FOREIGN PATENT DOCUMENTS

| | | |
|---|---|---|
| CN | 103479409 A | 1/2014 |
| CN | 102579116 B | 12/2015 |
| CN | 103732155 B | 9/2017 |
| DE | 102012100086 A1 | 8/2012 |
| EP | 1179994 B1 | 6/2006 |
| EP | 1772107 A1 | 11/2007 |
| EP | 2474271 A2 | 11/2012 |
| EP | 2736421 B1 | 6/2014 |
| EP | 2671517 B1 | 3/2017 |
| EP | 2741683 B1 | 7/2019 |
| JP | 2013255796 A | 12/2013 |
| WO | 2013055824 A1 | 4/2013 |
| WO | 2013130978 A2 | 9/2013 |
| WO | 2014058954 A2 | 4/2014 |
| WO | 2014120955 A1 | 8/2014 |

\* cited by examiner

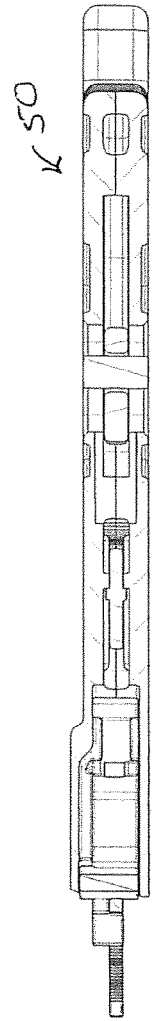
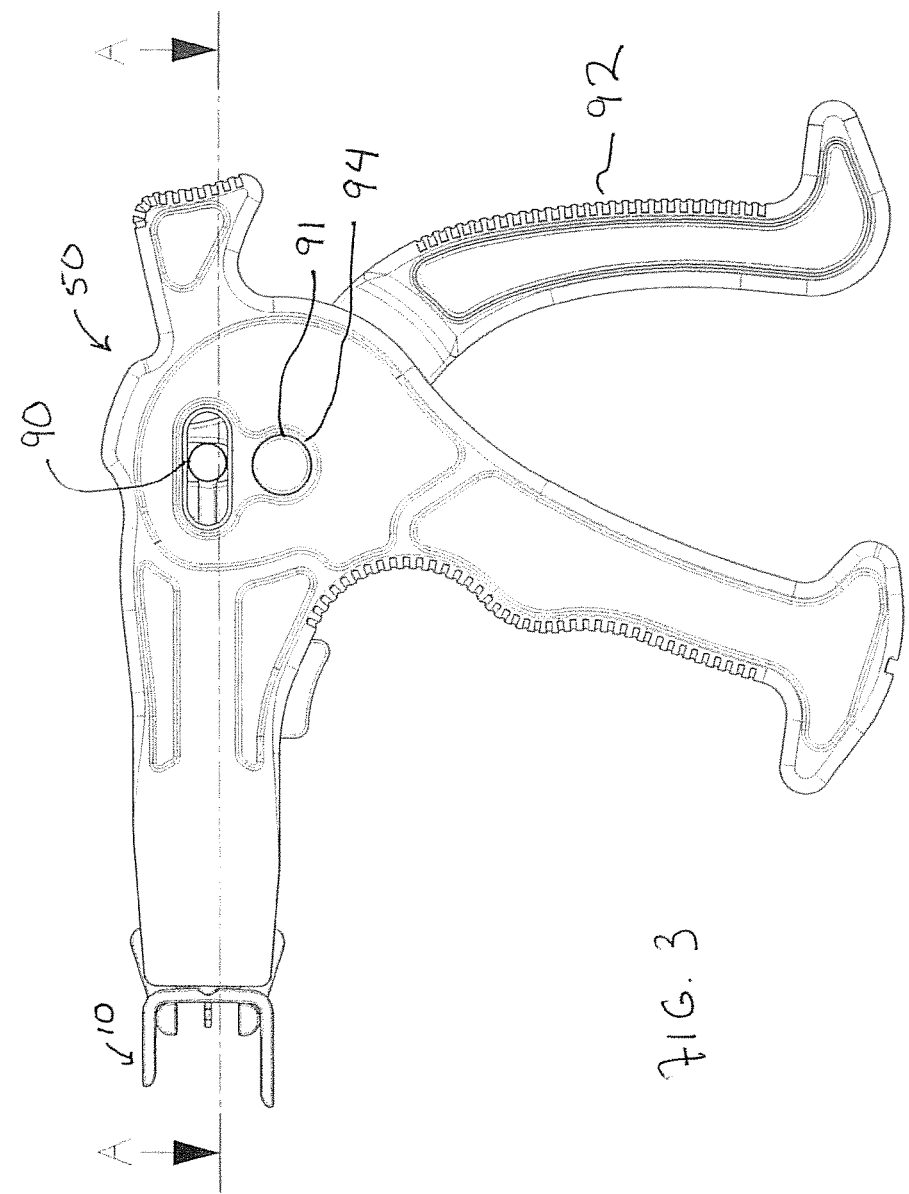

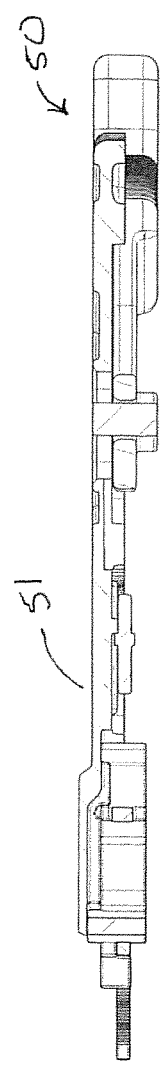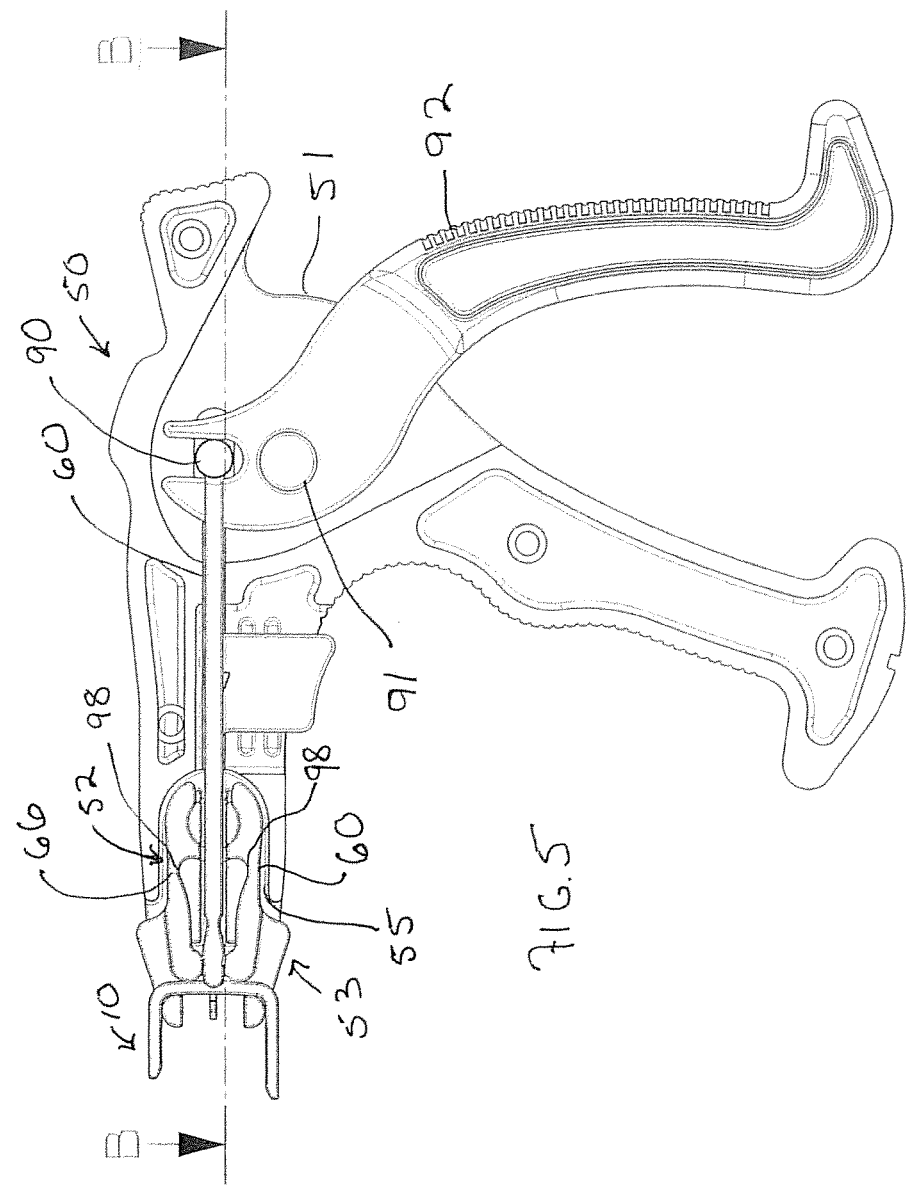

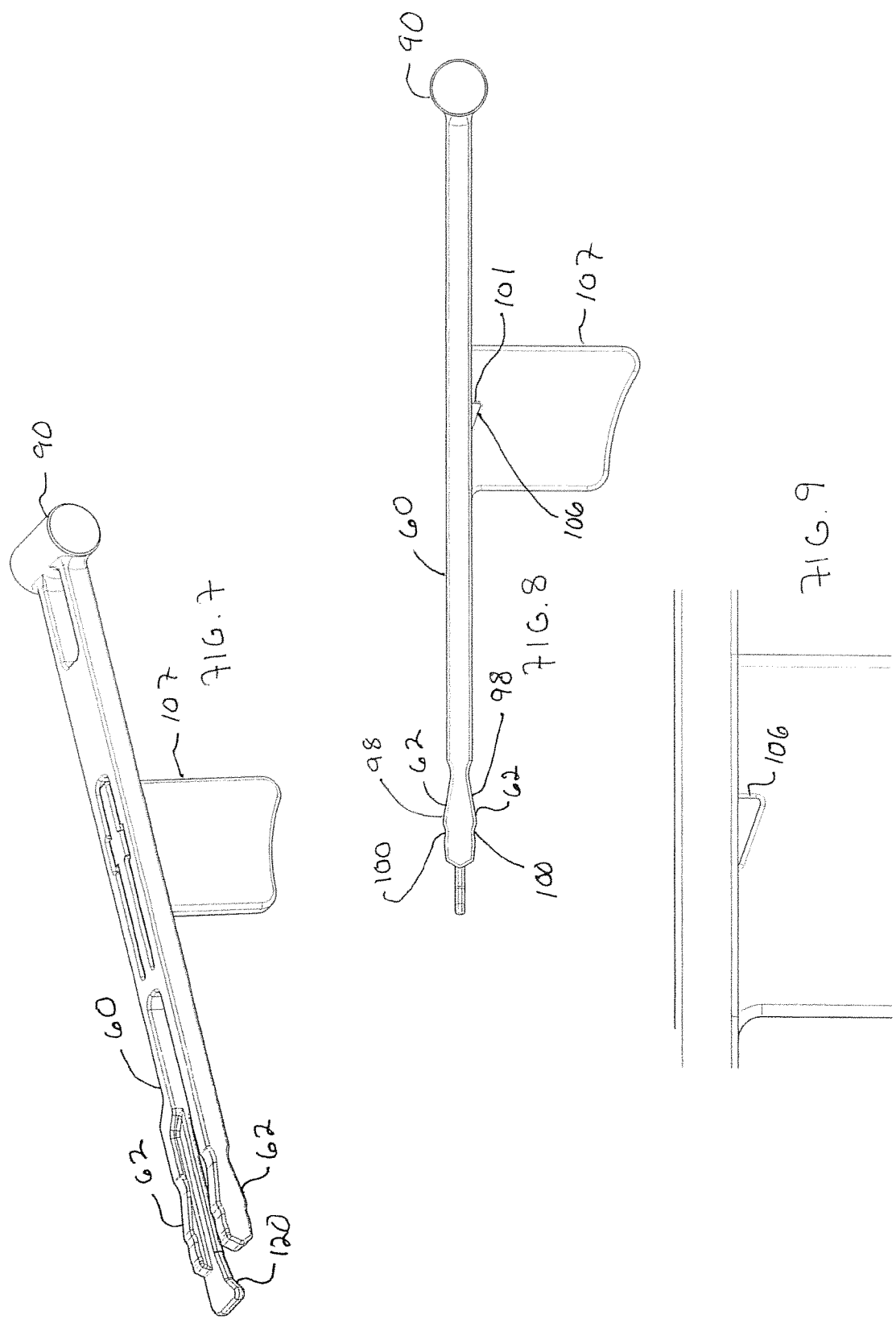

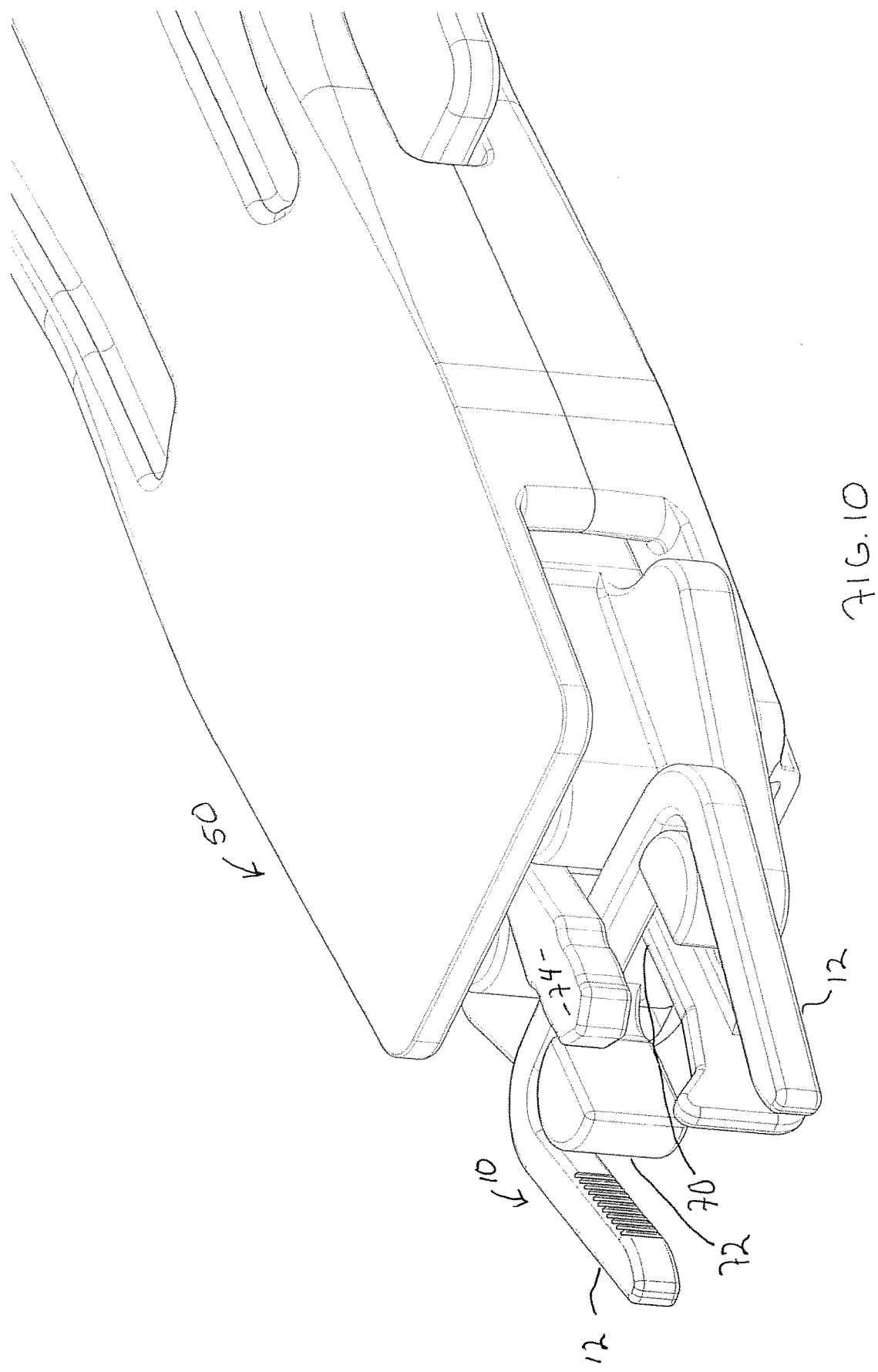

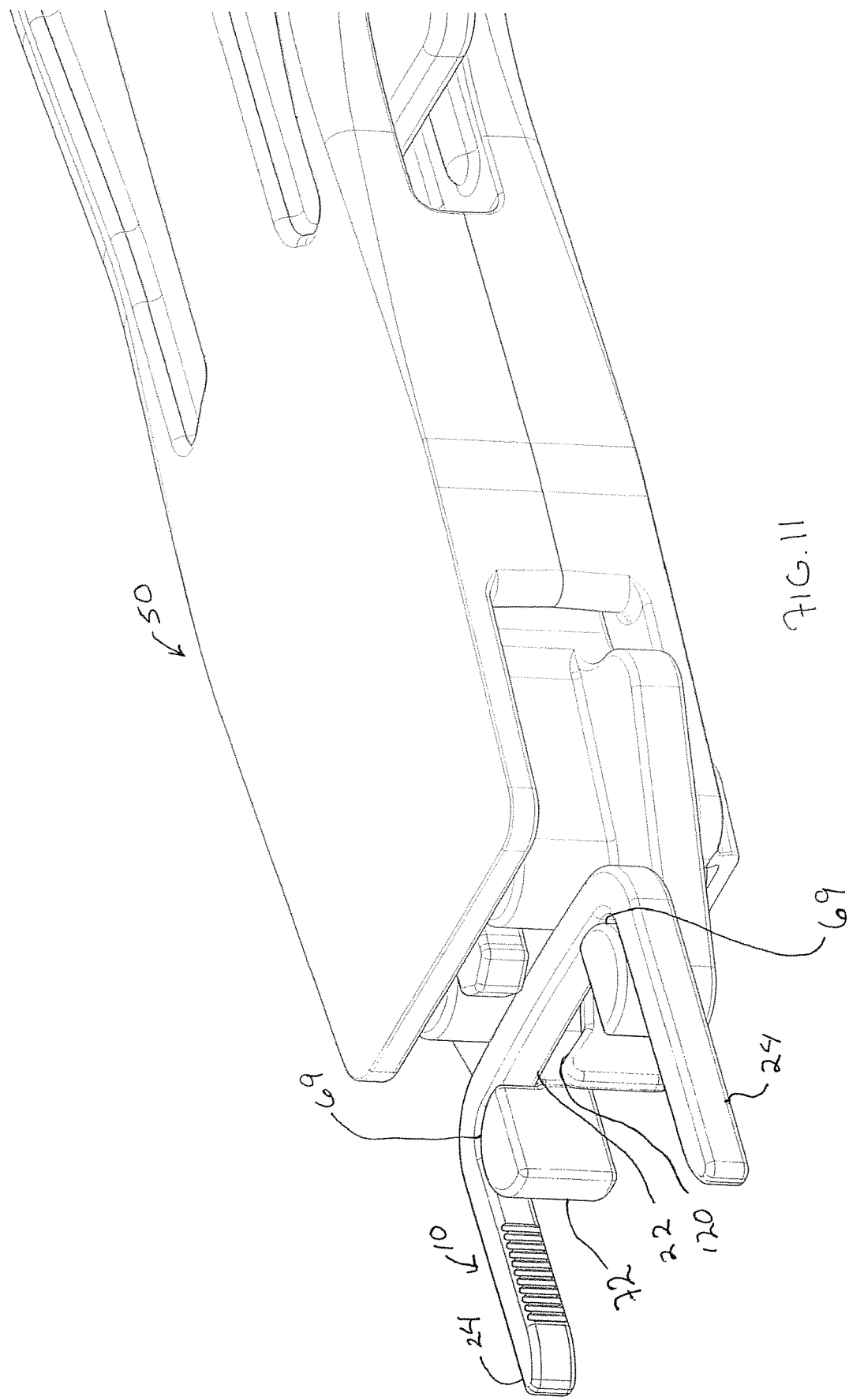

BONE STAPLE INSERTER

FIELD OF THE INVENTION

The invention comprises an inserter for use with a room temperature superelastic Nitinol staple intended for bone fixation in the surgical management of fractures and reconstruction of the foot and hand. The staple has a bridge member that extends a length along an axis and which joins legs spaced apart along the axis. The inserter can be used with a staple having two, three, or four legs (i.e. two pairs of legs spaced apart along the axis). The staple is fabricated in a closed (converging legs) shape and is mechanically deformed or "activated" by the inserter during use to induce the superelastic shape memory properties in the staple so as to compress bone segments and facilitate osteosynthesis in use. The staple is held on the inserter on cylindrical expanders and the inserter has a mechanism to spread the expanders which opens the legs so that the superelastic properties are induced and the legs are spread into transverse positions for implantation. The mechanism uses a trigger activated camming assembly which draws apart a pair of pivoting arm members. The staple is configured to accommodate fixation procedures in the forefoot, midfoot, rearfoot and hand, and the disposable inserter allows implantation of the staple in bone in a surgical procedure so as to apply a compressive force across a division of bone segments.

BACKGROUND OF THE INVENTION

Over 1.8 million orthopaedic trauma fixation procedures were performed in the US in 2016, and the market is expected to reach over $4 billion by 2025. The fastest growing part of the market is the staple fixation segment, which is also expected to remain the fastest growing through to 2025. The primary drivers for growth are reportedly a reduced operating time as compared to screws, and plates.

While the state of the art has advanced the use of bone staples, there remain issues in the use and design of the deployment instrument or inserter. In particular, the inserter needs to be capable of single handed use, and needs to be able to deform the staple to cause the superelastic deformation, while permitting easy and reliable deployment of the staple in bone. The design is intended for single use so that cost consideration, drawing in materials and manufacturing methods that meet economic requirements while presenting a design that is sufficiently strong to reliably accomplish the job. This means that the inserter provides that the staple can be deformed, inserted into pre-drilled pilot holes and tamped into position across a bone divide, all in a design that is quick, reliable, and easy to use, and advantageously single-handedly.

SUMMARY OF THE INVENTION

The invention provides an inserter for a superelastic compressive bone staple. A preferably configuration for the bone staple is a substantially U-shaped staple, i.e. a staple having a transverse bridge member and downwardly extending legs, which can be biased into a parallel "activated position" for insertion into the bone, and then released into a compressive configuration. Thus, the inserter is advantageously pre-assembled (i.e. prior to surgery) with a "U-shaped" or modified "table top" style staple in a non-activated state (i.e. in which the legs converge toward each other, each at an angle of from 60° to 88°, and preferably at an angle from 70° to 85° relative to an axis along the bridge member of the staple) and includes an easy to use mechanism for "activating" the staple by deforming the legs to a transverse position and initiating the super elastic properties of the staple material.

Prior to the deployment of the staple, the inserter holds the staple so that it is constrained on the bottom side at the corners of the bridge member where the legs join the bridge member and on the top side in a more central portion of the bridge member. The staple member is also secured laterally against the handle housing on one edge of the bridge member and against a distal tip of the disengagement trigger rod on the other lateral side. In particular, the staple securing mechanism of the inserter includes integrated functional components including an expander with top and bottom arm members that having jaws biased inward with cam followers that ride on a separate ramp joined to the disengagement trigger rod that is operably connected to a pivoting activation trigger which pivots relative to a handle housing assembly.

The disengagement trigger includes a finger activated trigger that can be pulled to release the staple from the inserter, and the activation trigger is activated by squeezing the trigger toward an opposing housing handle. As the trigger rotates about the pivot point in the handle casings, the ramp component is drawn backwards, which moves the expander component arms outwards to open the staple legs to the parallel position.

The pivoting of the activation trigger draws the disengagement trigger rod back in the handle housing which causes the cam followers on an expander member to follow a ramp on the trigger rod and to splay apart. The expander member includes expander arms include tailored deflection points to allow the arms to deflect at desired points. At a distal end, the expander member has a pair of rounded bosses that engage a top bridge member edge of the paired staple, and an opposed pair of cylindrical expander pins that engage the inside of the staple at the bottom surface of the bridge member and at the insides of the opposing legs. The expander pins are engaged by a scissoring mechanism having opposing members that open apart in response to being drawn back and over a camming mechanism. The opposing followers which are biased closed, scissor apart as they encounter the widening cam and the expanders separate to apply a corresponding force at the corners of the staple and accordingly to open the legs to 90°. The cylindrical pins work with staples having one or more legs on a side (so for two, three, or four, or even more lateral legs).

In accordance with the invention, a staple is supplied preassembled (on a disposable inserter) as part of a sterile packed procedure kit. The staple is not pre-loaded, which means that the staple is not subjected to the mechanical deformation which initiates the superelastic characteristics of the staple. The staple introducer provides quick and efficient use with minimal user interaction which is accomplished by constraining the staple on the inserter on the pair of cylindrical pins which form a part of an expander component of the inserter and which expands the staple legs to a 90° insertion position. The staple is further captured on the inserter and prevented from inadvertent disassembly from the inserter by a ramp that acts as a cover in the resting or non-energised position.

The cylindrical expander pins of the inserter retain the staple in a non-preloaded/non-energized position but interface with the staple in the proximal corners. This captures the staple securely on the inserter, and permits the activation of the staple for deployment. The design also enables use of the inserter with both symmetrical and asymmetrical leg staples. Moreover, retaining the staple in the proximal corners also ensures that the majority of the staple leg length is available for inserting on to the bones prior to low profile as possible to minimize packaging footprint and to prevent impingement with surrounding anatomy during use.

BRIEF DESCRIPTION OF THE DRAWINGS

FIG. 3 shows a side view of the staple inserter of FIG. 1;

FIG. 4 shows a cross-section of the staple inserter of FIG. 3 taken at line A-A;

FIG. 5 shows a side view of the staple inserter and staple with the front half of the handle housing member removed to show the deployment mechanism;

FIG. 6 shows a cross-section of the staple inserter of FIG. 5 taken at line B-B;

FIG. 7 is a side top view of the trigger rod of the present invention;

FIG. 8 is a side view of the trigger rod of the present invention;

FIG. 9 is a side detail of the deployment detent of the trigger rod of the present invention;

FIG. 10 is a front top view detail showing a staple preassembled on the inserter of FIG. 1 with the staple in the resting (non-energized, converging staple legs) position; and FIG. 11 is a view of the detail showing the preassembled staple of FIG. 10 with the staple in the energized position for implantation;

DETAILED DESCRIPTION OF THE INVENTION

Figure 1:
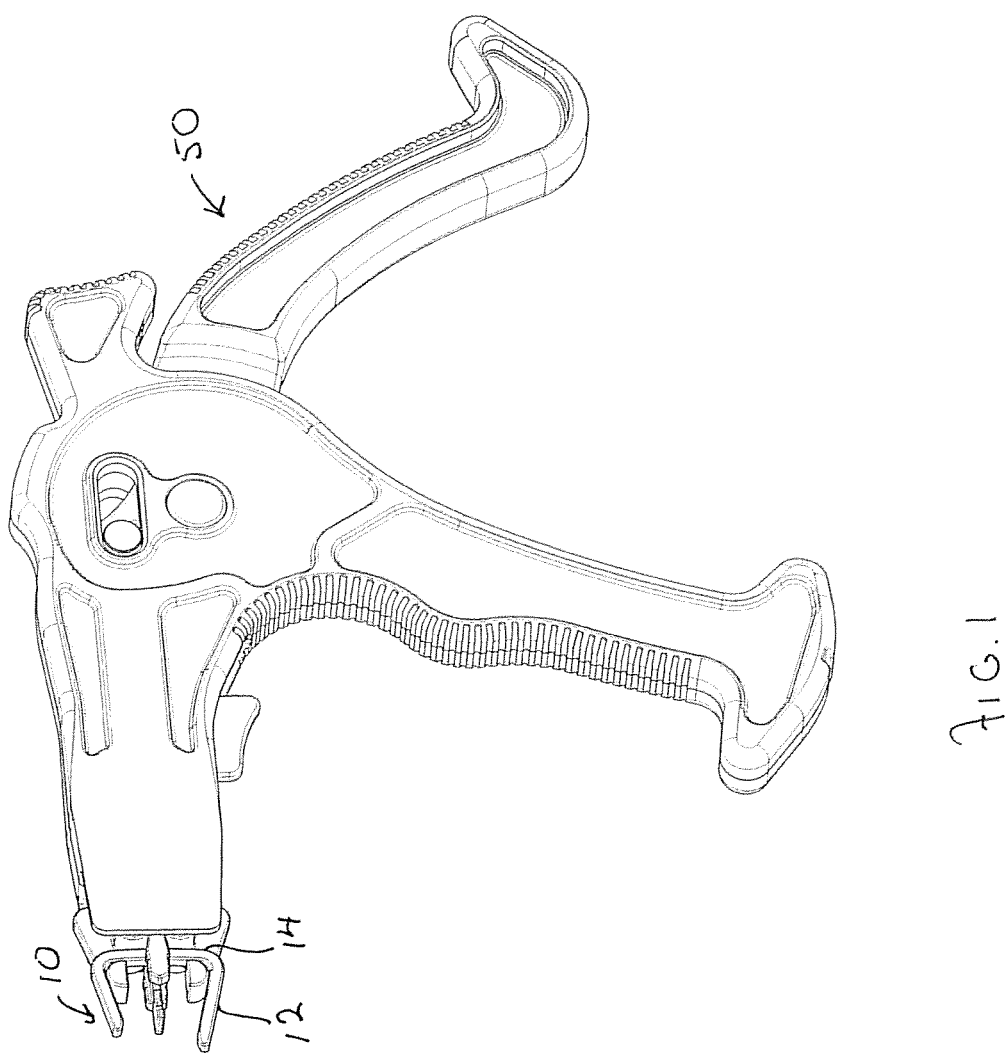
FIG. 1 shows a front side view of the staple inserter with a staple in accordance with the present invention.
Figure 2:
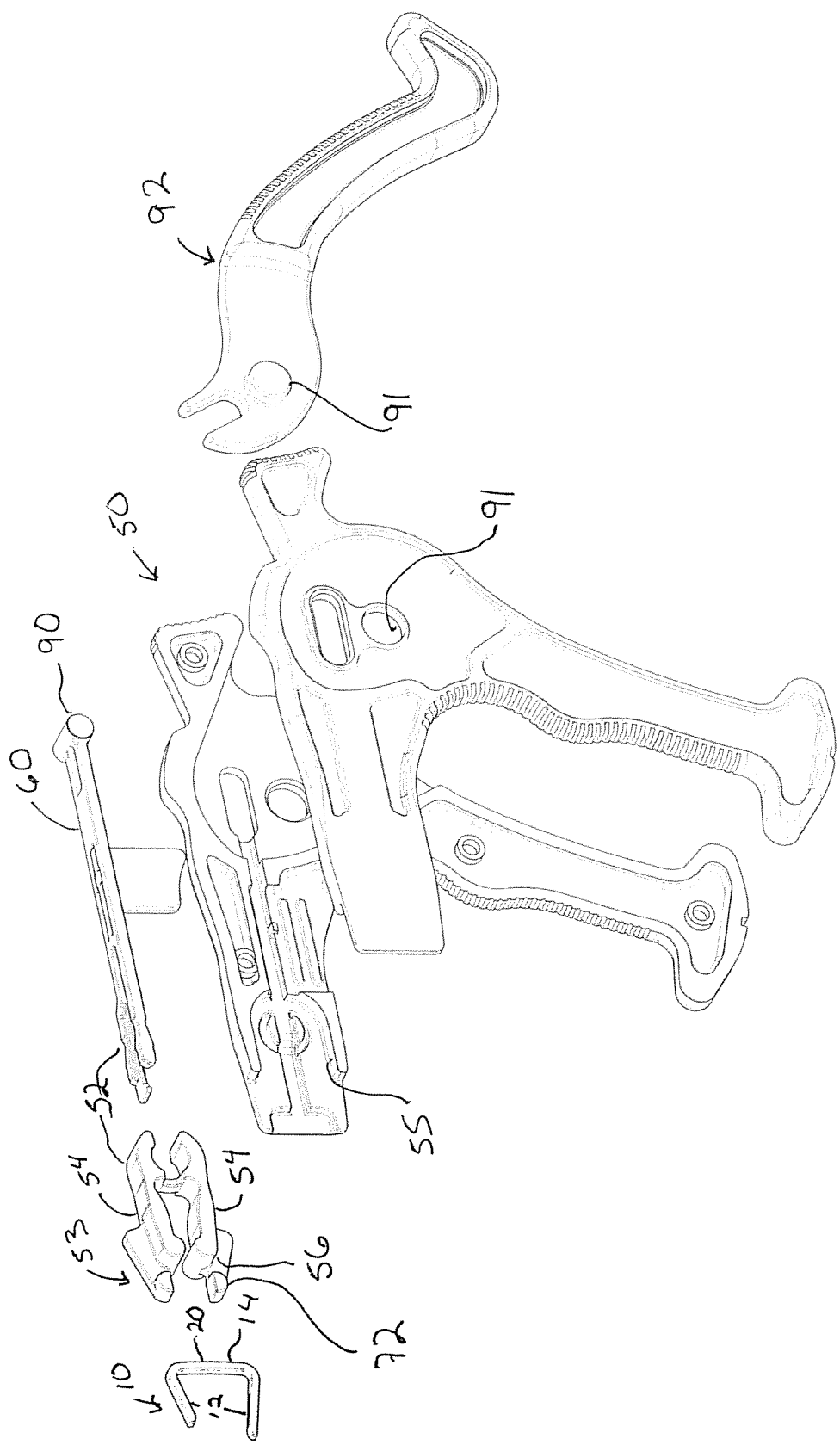
FIG. 2 shows an exploded view of the staple inserter of FIG. 1.

The product comprises an inserter 50 for use with a room temperature superelastic Nitinol compression staple 10 for bone fixation in the surgical management of fractures and reconstruction of the foot and hand. Typically, the staples used with the present invention have a nominally U-shaped profile with a bridge member 14 spanning a space between opposing legs 12 (and it should be understood that the present inserter is also suitable for use with a staple having four legs in which each end of the bridge member includes a pair of legs, or alternatively, the staple could have three legs with a pair on one end, and a single leg opposing the pair.)

The staple 10 has two or more, and preferably 2, 3, or 4 transversely extending legs 12 that will engage bones or bone segments through the cortical surfaces. The legs 12 are spaced apart from each other and joined together by bridge member 14 that extends across the area between legs at either end of the bridge member 14. As shown, the legs are joined to transitional extensions 16 which fold or curve at an angle of from 75° to 90°, and preferably from 85° to 90°.

The bridge member 14 has a top surface 20 and a bottom surface 22 which have corresponding shapes so that they are separated by a constant thickness for at least a portion, and preferably for at least 50%, and more preferably for at least 75% or even 90% of the surface area has a complex curving configuration. It extends along an axis preferably in a straight profile, but with a topography that curves in two dimensions. The shape includes two side edges 24, which may have an inwardly curving shape or may be represented by straight lines.

The staple is comprised of a material is elastic and has the ability to recover an original un-deformed shape so as to apply a compressive force. An example of a suitable material is a superelastic material which is activated into the superelastic state by mechanical deformation. Thus, the inserter 50 has a housing assembly 51 that is formed, such as by molding a plastic material into an integrated housing with functional components which are operatively connected to a deformation mechanism 52 to deform the legs 12 into a parallel alignment for insertion into pre-drilled holes in the bone or bones. In particular, the deformation mechanism includes an expander mechanism 53 is slidably held in a recess 55 in the housing 51 having arm members 54 that include distal jaws 56 with cam followers 58. The cam followers 58 are dragged backward on a trigger rod 60 which includes a ramp 62 of increasing width. This causes the arms 54 to deflect outwardly at proximal narrowed deflection points 66 in response to the widening pressure on the axially inward edges 68 of cam followers 58 on the expander member 53. Distal edges 67 of the cam followers 58 engage the top surface 20 of the staple bridge member 14 to hold the staple 10 on the top side, while the inner corner of the bridge/leg join is engaged on the bottom of the bridge member 14 and the inside of the leg member by the proximal surface of cylindrical pins. The staple 10 is held laterally on the inserter 50 by a lateral surface 70 of the expander member 53 which joins the cam followers 58 and the cylindrical pins 72 together, and also by a distal extension 74 of the trigger rod 60 which laps over the lateral edge of the staple bridge member 14 in the pre-assembled position.

Figure 12:
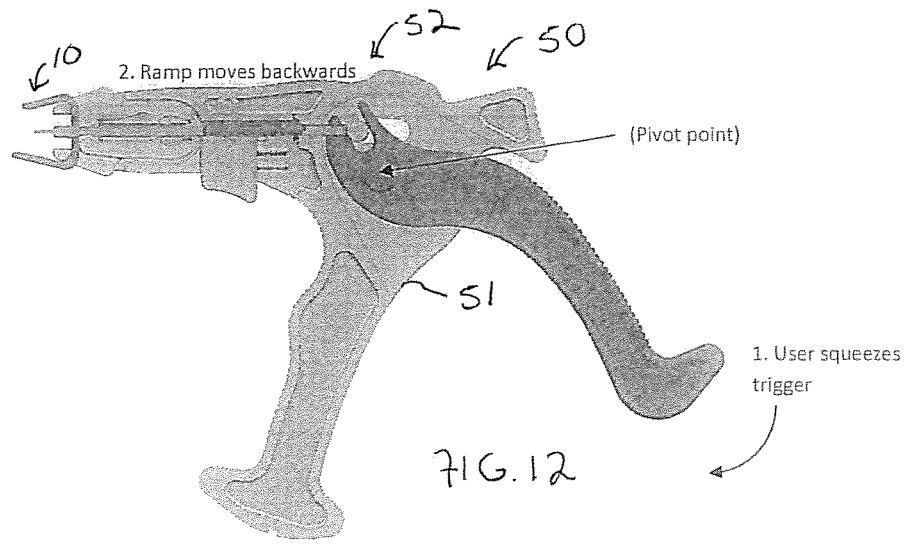
FIGS. 12, 13 and 14 illustrate the use of the trigger initiated activation mechanism with the backward motion of the trigger rod in response to the squeezing of the activation trigger toward the handle.
Figure 13:
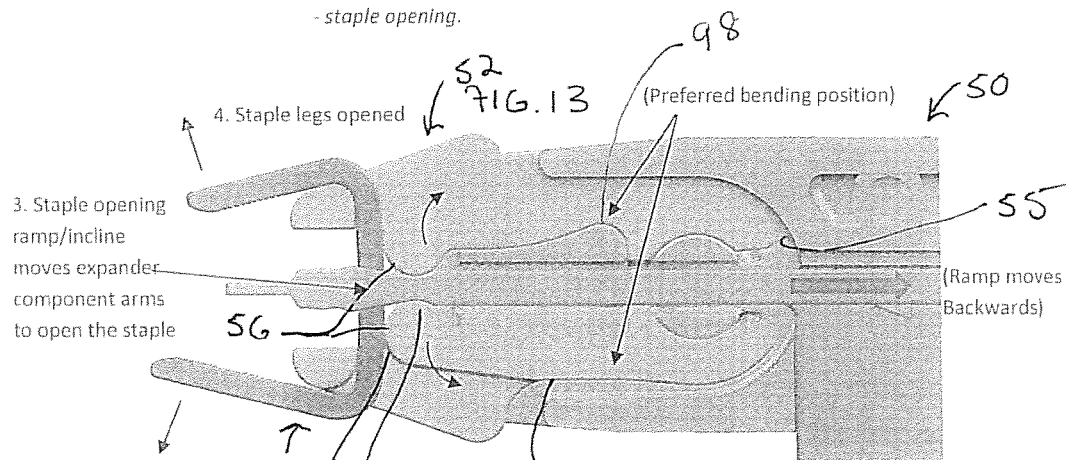
Figure 14:
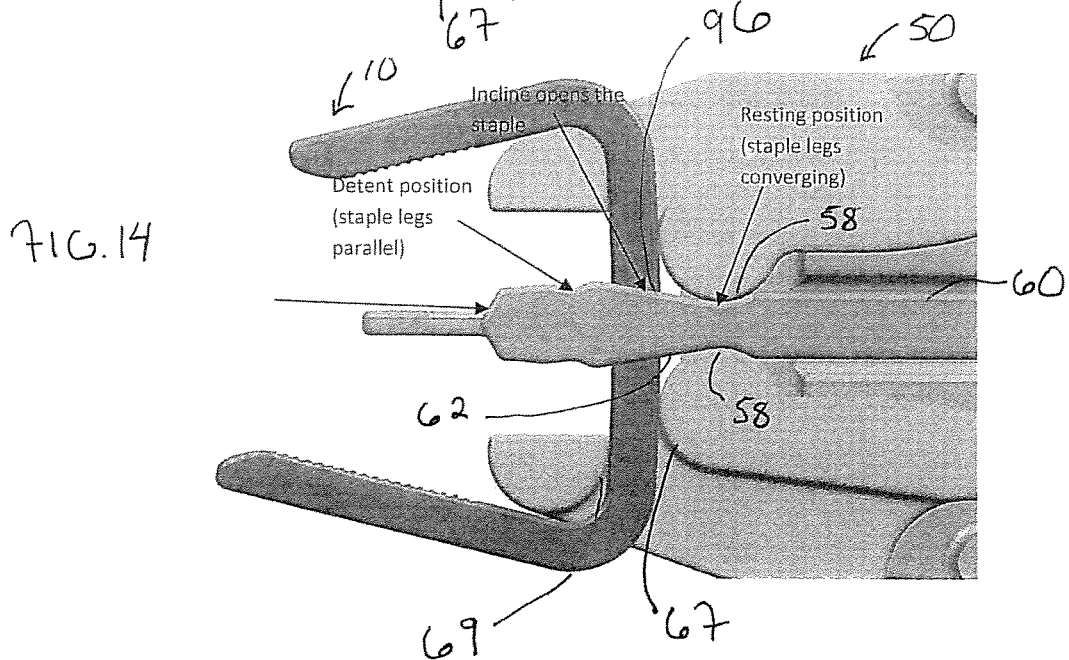

The operation of the inserter 50 for implantation of the compression staple is described as follows:

After the bone segments to be fused are prepared for receiving the compression staple 10, the user squeezes the activation trigger 90 to open the staple legs 12 to the parallel position ready for implantation. As the activation trigger 92 rotates about the pivot point 91 assembly in the handle casings 94, the trigger rod 60 bearing the ramp component 96 is drawn backwards, which moves the expander component arms 54 outwards to open the staple legs 12 to the parallel position (see FIGS. 12-14). The staple is fabricated in the closed (converging legs) shape and is mechanically deformed by the inserter 50 during use to induce the superelastic shape memory properties to compress bone segments and facilitate osteosynthesis. FIG. 13 shows the staple legs 12 opening as the ramp/incline 96 moves the expander arms 54 to an open position to open the staple legs 12 to a parallel position.

FIG. 13 shows that the arms 54 of the expander component 52 neck in at a deflection point 98 to a preferred bending position to facilitate opening and thus minimize additional forces in the system that have to be overcome to open the staple. The opening ramp 60 has a detent position 100 at the end of the incline section to provide tactile feedback to the user and a transient stopping position indicating to insert the parallel staple legs 12 into the bone segments as shown in FIG. 11.

Figure 15:
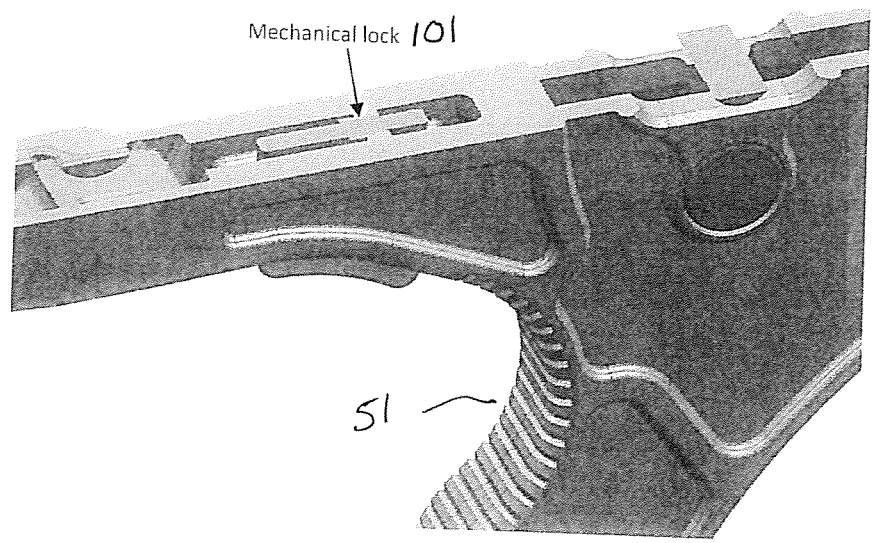
FIGS. 15 and 16 (a) and 16(b) illustrate a locking mechanism to retain the trigger rod in a position that secures the activated staple on the inserter until the user is ready to disengage the staple from the inserter.
Figures 16A, 16B:
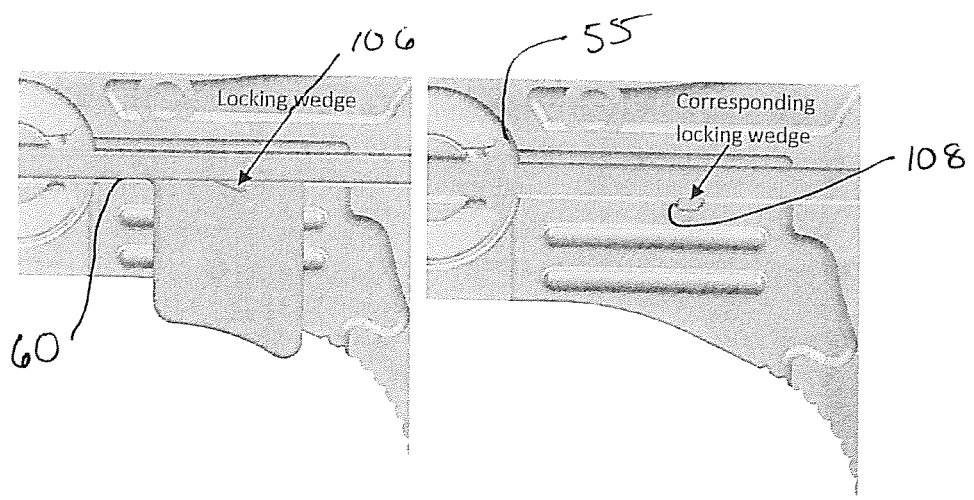
Figure 17:
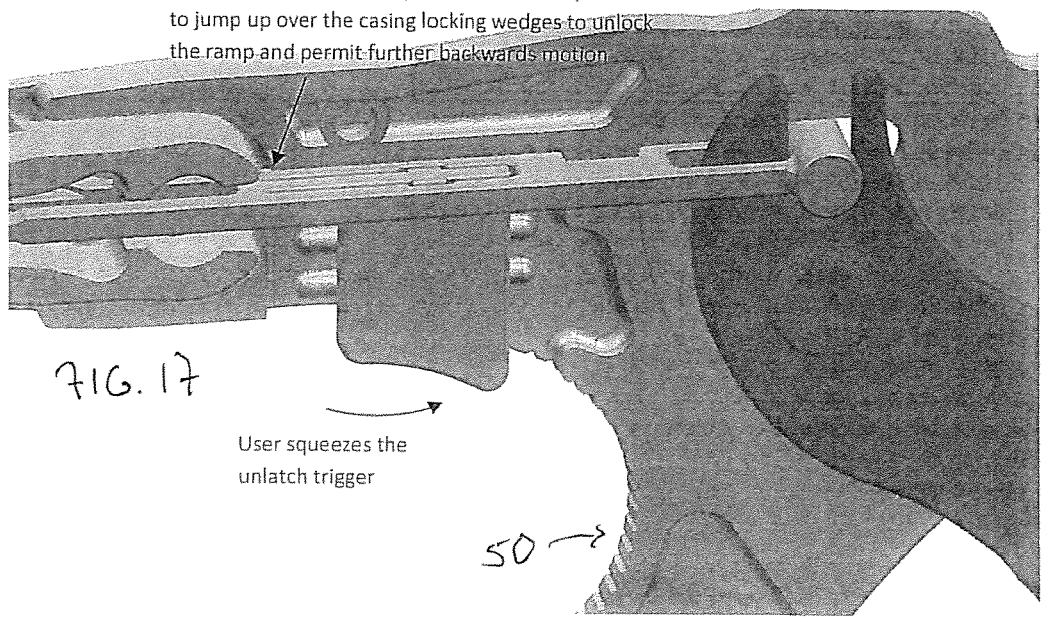
FIG. 17 is a detail illustrating the unlocking of the locking mechanism which permits the staple to be released from the inserter.
Figure 18:
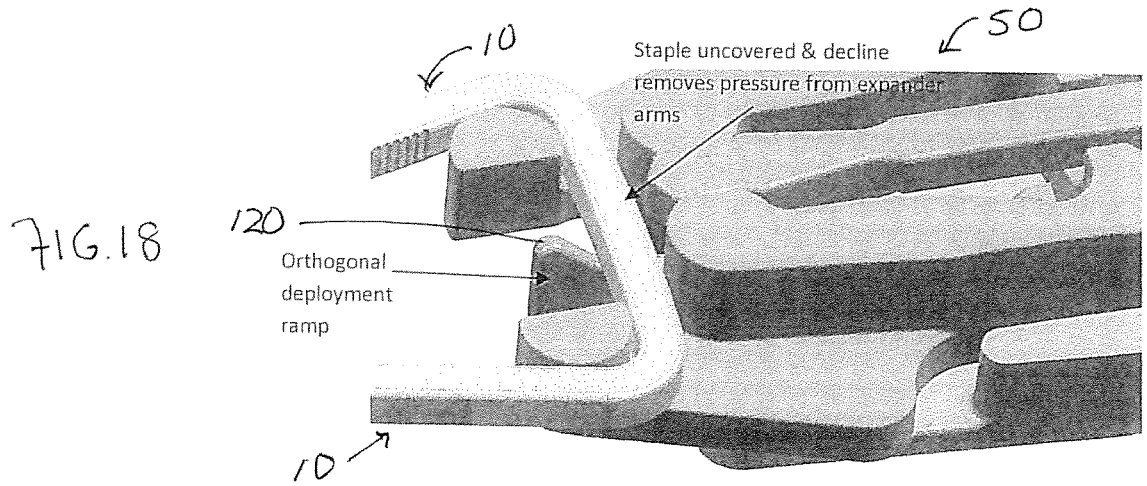
FIG. 18 illustrates a bottom side view of a detail showing the deployment mechanism of the expander component.
Figure 19:
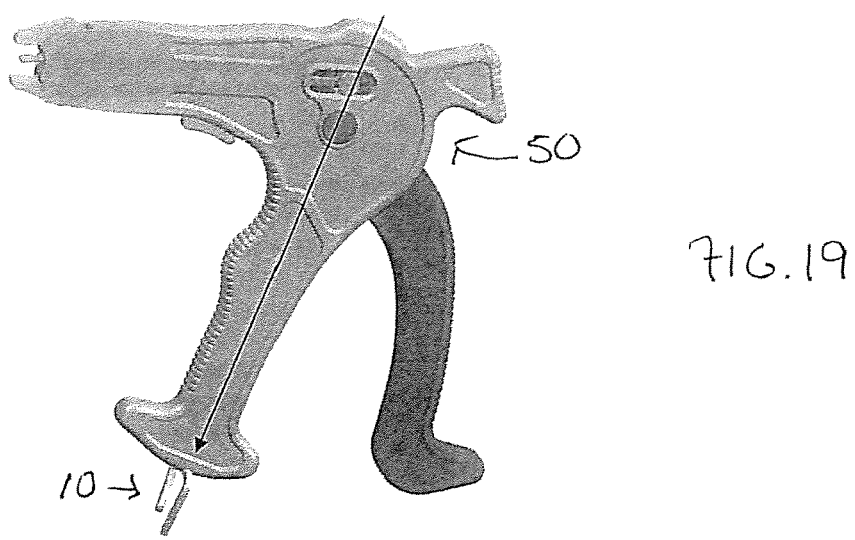
FIG. 19 illustrates the use of the inserter to tamp the staple into a final position.

Due to the inertial forces as the user squeezes the trigger, a mechanical lock assembly 101 may also be utilized in addition to the ramp detent 100 to ensure that the staple 10 is not inadvertently deployed before being inserted into the bones. The mechanical lock assembly 101 may be embodied in numerous ways, a preferred method that is likely highly intuitive to the user is depicted in FIGS. 15 and 16 (a) and b). A locking wedge 106 is situated on each side of the ramp component. As the staple is opened, the locking wedge 106 engages the corresponding locking wedges 108 in each handle case, which stops any further backwards motion of the ramp component, thus preventing premature deployment of the staple. The action of the locking mechanism coincides with the ramp detent 100 at the position where the staple legs are parallel and ready to be implanted.

At this point, the user inserts the staple 10 into the bone segments to be fused, the mechanical lock 106 is then released to permit staple release by squeezing the ramp component 107 with the index finger (see FIG. 15). The lock section of the ramp component 108 deflects upwards to unlatch the ramp locking wedges 106 from the lock wedges 108 in the handle casings, and the user continues to squeeze pull the ramp back to the final deployment position.

As the ramp moves backwards, the ramp removes the force from the expander arms and accordingly the expander pins, and as the stroke is completed the staple is uncovered by the side of the ramp that was preventing escape and an orthogonally orientated deployment section 120 pushes the staple off the expander pins as shown in FIG. 11. (Since the staple legs are in the bones at this point, the deployment ramp moves the pins off the staple rather than pushing the staple off the pins). Thus, in a single stroke of the deployment mechanism, the staple is both activated to spread the legs to a parallel position and actively disengaged from the inserter. It is envisioned that other means of disengagement could be used with the expander mechanism of the present invention, for example, a rotatable mechanism could be used in which the lateral holding mechanism were free to one side of the staple or on opposing lateral edges of the staple to allow the staple to be disengaged either be rotating the inserter about an axis parallel to the bridge of the staple or parallel to the open legs of the staple.

A known risk with the prior art staples is associated with over-spreading the staple, which can over-stress the staple legs and have a deleterious effect on mechanical properties, recoverable strain and fatigue resistance. However, the present invention reduces this risk through material improvements in the staple and in the inserter staple deployment mechanism. The staple and staple inserter are designed to function together to avoid over-spreading and/or misalignment of the staple legs to reduce potential use risks and to provide a device which is inherently less prone to user error.

The staple inserter of the present invention is suitable for manufacture via injection moulding, but could also be fabricated from other manufacturing techniques such as, but not limited to, machined, 3-d printed or stamped components. The inserter can be fabricated from plastic or metal materials, or a combination of both.

The staple and inserter are configured to accommodate different fixation procedures in the forefoot, midfoot, rearfoot and hand, and the inserter allows implantation of the staple in bone in a surgical procedure so as to apply a compressive force across a division of bone segments for fracture and osteotomy fixation of the hand and foot, including joint arthrodesis and to stabilize and dynamically compress bone fragments to facilitate osteosynthesis.

What is claimed is:

1. A staple inserter, comprising:
a handle and an activation trigger which is operably joined to a pair of pins spaced a distance a and capable of holding a staple having a pair of legs spaced apart a distance a and connected by a bridge member, and an expander mechanism which includes a trigger rod and is activated by the activation trigger, the expander mechanism including a ramp surface that engages a pair of followers joined to the pair of pins where the activation trigger is linked to the followers to draw the followers along the ramp surface to increase to increase the distance a and the trigger rod further comprises distal edges that are capable of securing the bridge member on a top side of the bridge member and the pins are capable of securing the legs on surfaces of the legs which oppose each other.

2. A staple inserter as set forth in claim 1, wherein the trigger rod further includes a detent that provides a tactile indication that the staple legs are parallel.

3. A staple inserter as set forth in claim 2, wherein the trigger rod further includes a deployment ramp distal to the detent.

4. A staple inserter as set forth in claim 3, wherein the staple is constrained on a lateral edge of the bridge member by a distal tip of the trigger rod.

5. A staple inserter as set forth in claim 1, wherein the pins are hemicylindrical.

6. A staple inserter as set forth in claim 1, wherein the bridge member of the staple is engaged by a holding member prior to disengagement.

7. A staple inserter as set forth in claim 6, wherein the bridge member has a top surface that is engaged by the holding member.

8. A staple member as set forth in claim 7, wherein the staple member bridge member has two lateral edges and includes a center point along the length and a holding member engages one lateral edge on one side of the center point and a second holding member engages a second lateral edge on an opposing side of the center point.

9. A staple member as set forth in claim 1, wherein the staple member bridge member has two lateral edges and includes a center point along the length and a holding member engages one lateral edge on one side of the center point and a second holding member engages a second lateral edge on an opposing side of the center point.

10. A staple inserter, comprising:
a handle, a staple holding mechanism capable of holding a staple having a pair of legs spaced apart a distance a and connected by a bridge member, and an deployment mechanism that includes an activation trigger which is operably joined by a trigger rod to an expander mechanism which is activated by the activation trigger, and the expander mechanism including a ramp surface that engages a pair of followers where the activation trigger is linked to the followers to draw the followers along the ramp surface the expander mechanism activated by the activation trigger draws the followers along the ramp to increase to increase the distance a and to disengage the staple from the holding mechanism and the trigger rod further comprises distal edges that are capable of securing the bridge member on a top side of the bridge member and the holding mechanism includes pins that are capable of securing the legs on surfaces of the legs which oppose each other.

11. A staple inserter as set forth in claim 10, wherein the inserter further includes a trigger rod that links the followers to the activation trigger.

12. A staple inserter as set forth in claim 11, wherein the bridge member of the staple is engaged by the holding member prior to disengagement.

13. A staple inserter as set forth in claim 11, wherein the bridge member has a top surface that is engaged by the holding member.

14. A staple inserter as set forth in claim 10, wherein the trigger rod further includes a detent that provides a tactile indication that the staple legs are parallel.

15. A staple inserter as set forth in claim 14, wherein the trigger rod further includes a deployment ramp distal to the detent.

16. A staple inserter as set forth in claim 15, wherein the staple is constrained on a lateral edge of the bridge member by a distal tip of the trigger rod.

17. A staple inserter as set forth in claim 10, wherein the pins are hemicylindrical.

\* \* \* \* \*